United States Patent [19]

Haruna et al.

[11] Patent Number: 4,663,459

[45] Date of Patent: May 5, 1987

[54] METHOD FOR PREPARING 2,2,6,6-TETRAMETHYL-4-OXOPIPERIDINE

[75] Inventors: Tohru Haruna, Saitama; Atsushi Nishimura, Washinomiya; Kazuo Sugibuchi, Tokyo, all of Japan

[73] Assignee: Adeka Argus Chemical Co., Ltd., Urawa City, Japan

[21] Appl. No.: 701,475

[22] Filed: Feb. 14, 1985

[30] Foreign Application Priority Data

Feb. 16, 1984 [JP] Japan ................................. 59-27712

[51] Int. Cl.$^4$ .......................................... C07D 211/74
[52] U.S. Cl. .................................................. 546/242
[58] Field of Search ........................................ 546/242

[56] References Cited

U.S. PATENT DOCUMENTS

| | | | |
|---|---|---|---|
| 3,513,170 | 5/1970 | Murayama et al. | 546/242 |
| 3,953,459 | 4/1976 | Orban et al. | 546/242 |
| 3,959,295 | 5/1976 | Orban et al. | 546/242 |
| 4,252,958 | 2/1981 | Hirai et al. | 546/242 |

Primary Examiner—John M. Ford
Assistant Examiner—Kurt G. Briscoe

[57] ABSTRACT

A process is provided for the preparation of 2,2,6,6-tetramethyl-4-oxopiperidine, reacting acetone with ammonia in the presence of a catalytically effective amount of an organic carboxylic acid halide.

17 Claims, No Drawings

METHOD FOR PREPARING 2,2,6,6-TETRAMETHYL-4-OXOPIPERIDINE 2,2,6,6-tetramethyl-a4-oxopiperidine, triacetone amine, is prepared by reacting acetone with 2,2,4,4,6-pentamethyl-2,3,4,5-tetrahydropyrimidine(acetonine). Triacetone amine has been recognized as a key intermediate in the preparation of 2,2,6,6-tetramethyl piperidyl and related light stabilizers for polymer materials.

Several procedures for reacting acetone with acetonine are described in the patents and literature.

W. Heinz Annalen der Chemie 203 336 (1880) converts acetone to phorone in about 30% yield, and reacts phorone with ammonia to form triacetone amine in 70% yield.

H. K. Hall Journal of the American Chemical Society 79 5447 (1957) reacts acetone with ammonia in the presence of calcium chloride for 7 days, obtaining triacetone amine in about 20% yield, after careful fractional distillation to separate the desired product from a different basic nitrogen compound having a near boiling point.

K. Murayama U.S. Pat. No. 3,513,170 patented May 19, 1970 converts 2,2,4,4,6-pentamethyl-2,3,4,5,-tetrahydropyrimidine(acetonine) to triacetone amine reaction with a Lewis acid in the presence of water.

I. Orban U.S. Pat. No. 3,959,295, patented May 25, 1978 prepares triacetone amine from acetone and ammonia in the presence of acidic catalysts in two stages, carried out at two different temperatures, with the amount of acetone in the second stage being at least 1.6 moles per mole of ammonia.

In accordance with this invention, triacetone amine is prepared by a catalytic process from acetone and ammonia. Acetone and ammonia are reacted in the presence of a catalytically effective amount of an organic carboxylic acid halide, and triacetone amine recovered from the reaction mixture.

Only a small amount of catalytically effective organic carboxylic acid halide is required. As little as 0.01% by weight of the acetone is effective. Preferably, the amount is within the range from about 0.05% to about 10% by weight of the acetone. Larger amounts can be used but tend to be wasteful and uneconomic.

The organic carboxylic acid halide catalysts of this invention are mono or di carboxylic acid halides having from two to about eighteen carbon atoms, and the organic group may be substituted with halogen. They are defined by the formula:

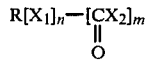

$$R[X_1]_n-[CX_2]_m$$
$$\parallel$$
$$O$$

in which:
R is a hydrocarbon readical selected from the group consisting of aliphatic, cycloaliphatic and aromatic radicals having from one to about seventeen carbon atoms;
$X_1$ and $X_2$ are halogen, i.e., fluorine, chlorine, bromine, or iodine, and can be the same or different;
n is a number from 0 to 6; and
m is 1 to 2.

Exemplary R aliphatic hydrocarbon including methyl, ethyl, propyl, isopropyl, butyl, isobutyl, sec-butyl, tert-butyl, amyl, isoamyl, hexyl, isohexyl, tert-hexyl, heptyl, octyl, isooctyl, tert-octyl, 2-ethylhexyl, nonyl, isononyl, decyl, isodecyl, undecyl, dodecyl, tridecyl, tetradecyl heptadecyl, propenyl, butenyl, hexenyl, octenyl, nonenyl, heptadecenyl.

Exemplary R cycloaliphatic hydrocarbon include cyclopropyl, cyclobutyl, cyclopentyl, cyclohexyl, methyl cyclohexyl, cycloheptyl, cyclooctyl, cyclododecyl.

Exemplary R aromatic hydrocarbon include phenyl, naphthyl, phenanthryl and anthracenyl.

Exemplary organic acid halide catalysts are acetyl chloride, propionyl chloride, butyroyl chloride, octanoyl chloride, decanoyl chloride, lauroyl chloride, stearoyl chloride, diethylactyl chloride, acetyl bromide, acryloyl chloride, methacryloyl chloride, oxaloyl dichloride, adipoyl dichloride, sebacoyl dichloride, fumaroyl dichloride, chloroacetyl chloride, dichloroacetyl chloride, trichloroacetyl chloride, bromoacetyl bromide, 3-chloropropionyl chloride, 2 -bromopropionyl bromide, 2-bromopropionyl chloride, 2-bromoisobutyroyl bromide, 2-bromoisobutyroyl chloride, 2-bromo-2,2-diethylacetyl chloride, 2-bromo-2,2-diethylacetyl bromide, trifluoroacetyl chloride, 3,4-dichloroperfluoro butyroyl chloride, 3,5,6-trichloroperfluorohexanoyl chloride, 2-bromocaproyl chloride, 2-bromocaproyl chloride, 2-bromocapryloyl chloride, 2-bromononanoyl chloride, 2-bromolauroyl chloride, 2-bromopalmitoyl chloride, benzoyl chloride, benzoyl bromide, toluoyl chloride, 4-t-butylbenzoyl chloride, phthaloyl dichloride, isophthaloyl dichloride, terephthaloyl dichloride, mono and dichlorobenzoyl chloride, 2-chlorocinnamoyl chloride, cyclohexanoyl chloride.

The organic acid bromide catalysts and halogen substituted carboxylic acid halide catalysts are preferred.

In the process of this invention, acetone can be used as well as condensation products of acetone, such as diacetone alcohol, mesityl oxide, and phorone, as such or mixed with acetone.

A number of materials function as co-catalysts when combined with the catalyst of this invention, interacting beneficially to give synergistic results, better than with either alone.

Co-catalysts that can be used with the catalyst of this invention include elemental bromine and elemental iodine; lithium, sodium and potassium bromide and iodide; ammonium chloride, bromide and iodide; hydrazine chloride; lithium and ammonium thiocyanate; maleic hydrazide; barium hydroxide; synthetic absorbents such as magnesium silicate hydrate and aluminum silicate hydrate; boron trifluoride, zinc chloride and calcium chloride.

When a co-catalyst is used together with the catalyst of this invention, the amount of co-catalyst is usually within the range from about 0.01 to about 10% by weight of the acetone, preferably from about 0.1 to about 5%.

The relative proportions of acetone and ammonia can be varied over a wide range, from stoichiometric to a large excess of either. The molar ratio of acetone to ammonia can be within the range from about 1:1 to about 20:1, preferably from 2:1 to 10:1.

The reactants, catalyst, co-catalyst when used, solvent and other ingredients can be charged all at once, or in several increments, as the reaction proceeds.

Neither reaction temperature nor reaction pressure is critical. The process of the invention will proceed at room temperature or below, as well as at elevated temperatures. Preferably, the reaction temperature is within the range from about 0° C. and the boiling point of the reaction mixture at atmospheric pressure, with a range of from about 30° to about 60° C. particularly preferred. If the reaction mixture boils at 60° C. or below, the reaction temperature can be increased to from 60° C. to 110° C. by applying superatmospheric pressure up to about 30 atmospheres, preferably up to about 5 atmospheres.

A solvent or diluent is not necessary in the process of this invention, but can be used, if desired. The solvent should be inert, and have a boiling temperature at or above the selected reaction temperature. Solvent that can be used, for example, are aliphatic hydrocarbons, such as pentane, hexane, heptane; aromatic hydrocarbons such as benzene, toluene, xylene; chlorinated aliphatic and aromatic hydrocarbons, such as methylene chloride, trichloroethane, chloroform, carbon tetrachloride, chlorobenzene, the dichlorobenzenes and trichlorobenzenes; cycloaliphatic hydrocarbons such as cyclohexane; aliphatic and cycloaliphatic alcohols, such as methanol, ethanol, isopropanol, butanol, t-butanol, 2-ethylhexanol, cyclohexanol; aliphatic and heterocyclic ethers, such as diethyl ether, tetrahydrofurane and dioxane.

In the preparation of triacetone amine according to the process of this invention, water does not interfere. It is neither necessary to add water, nor to exclude it. Some water is formed as a product of the reaction between acetone and ammonia; such water can be removed as it forms, or be allowed to accumulate, and become part of the solvent system.

At the end of the reaction, the lowest boiling components of the mixture are unreacted acetone, water and solvent, if used; these can be stripped off and used as the solvent or diluent in subsequent preparations, without separation from one another.

Triacetone amine can be recovered from the reaction mixture by precipitation as the hydrate by adding water; or by precipitation as the hydrohalide, sulfate or oxalate salt by adding the appropriate acid; or by distillation, suitably after adding an excess of strong alkali, such as concentrated aqueous potassium or sodium hydroxide solution.

The following Examples represent preferred embodiments of the invention.

EXAMPLES 1 to 6

A flask equipped with a Dimroth condenser and a gas inlet tube was charged with acetone 180 g, methanol 9 g, and 1.8 g of the catalyst shown in Table I. Ammonia gas 12 g was then introduced over five hours at 15° to 20° C., while stirring. Then, the flow of ammonia gas was stopped, and the mixture was heated at 50° to 55° C. for 15 hours.

At the end of this time, the reaction mixture was stripped in vacuo, and the triacetone amine recovered by vacuum distillation. The results are shown in Table I.

TABLE I

| Example No. | Catalyst | Yield of Triacetone amine | | |
|---|---|---|---|---|
| | | g | %[1] | %[2] |
| Control 1 | Ammonium chloride | 31.9 | 29.2 | 52.5 |
| Control 2 | Acetic acid | 20.5 | 18.7 | 37.3 |
| Control 3 | Monochloroacetic acid | 23.6 | 21.6 | 41.5 |
| Example 1 | Acetyl chloride | 54.1 | 49.4 | 69.6 |
| Example 2 | Acetyl bromide | 64.2 | 58.7 | 75.0 |
| Example 3 | Monochloroacetyl chloride | 58.7 | 53.6 | 72.6 |
| Example 4 | Monobromoacetyl bromide | 72.5 | 66.3 | 79.5 |
| Example 5 | α-Bromopropionyl bromide | 69.2 | 63.2 | 77.7 |
| Example 6 | Benzoyl bromide | 60.6 | 55.4 | 72.9 |

[1] Based on ammonia used
[2] Based on acetone used

It is apparent that the catalysts of the invention gave much higher yields of triacetone amine than the prior art catalysts.

EXAMPLES 7 to 12

Into a mixture of 50 g acetone and 2.7 g of the catalyst shown in Table II was introduced ammonia gas 8.5 g over 4 hours at 15° to 20° C., with stirring. Acetone 130 g then was added, and the reaction mixture stirred for 15 hours at 50° to 55° C. The reaction mixture was worked up by distillation using the same procedure as in Examples 1 to 6. The results are shown in Table II.

TABLE II

| Example No. | Catalyst | Yield of Triacetone amine | | |
|---|---|---|---|---|
| | | g | %[1] | %[2] |
| Control 1 | Acetic acid | 33.7 | 43.5 | 61.4 |
| Control 2 | Monochloroacetic acid | 37.5 | 48.4 | 64.7 |
| Example 7 | Acetyl chloride | 44.0 | 56.8 | 73.8 |
| Example 8 | Acetyl bromide | 53.6 | 69.2 | 80.1 |
| Example 9 | Monochloroacetyl chloride | 47.4 | 61.2 | 76.6 |
| Example 10 | Monobromoacetyl bromide | 56.8 | 73.3 | 81.2 |
| Example 11 | Benzoyl bromide | 51.5 | 66.5 | 78.6 |
| Example 12 | Adipoyl dichloride | 43.2 | 55.7 | 73.0 |

[1] Based on ammonia used
[2] Based on acetone used

It is apparent that the catalysts of the invention gave much higher yields of triacetone amine than the prior art catalysts.

EXAMPLES 13 to 17

An autoclave was charged with 290 g of acetone, 17 g of ammonia gas and 2.9 g of the catalyst shown in Table III. Then, the mixture was allowed to react for seven hours at 70° C., while stirring. The reaction mixture was worked up as in Examples 1 to 6. The results are shown in Table III.

TABLE III

| Example No. | Catalyst | Yield of Triacetone amine | | |
|---|---|---|---|---|
| | | g | %[1] | %[2] |
| Control 1 | Ammonium chloride | 96.5 | 62.3 | 67.8 |
| Control 2 | Monochloroacetic acid | 85.7 | 55.3 | 62.0 |
| Example 13 | Monochloroacetyl chloride | 103.2 | 66.6 | 72.9 |
| Example 14 | Acetyl bromide | 110.0 | 71.0 | 76.6 |
| Example 15 | Monobromoacetyl bromide | 121.4 | 78.3 | 80.4 |
| Example 16 | α-Bromopropionyl bromide | 119.7 | 77.2 | 79.5 |
| Example 17 | Benzoyl bromide | 108.5 | 70.0 | 74.7 |

[1] Based on ammonia used
[2] Based on acetone used

It is apparent that the catalysts of the invention gave much higher yields of triacetone amine than the prior art catalysts.

EXAMPLES 18 to 21

These Examples show the effect of co-catalysts. Into a mixture of acetone 50 g, methanol 9 q, monobromoacetyl bromide 0.9 g, and the co-catalyst as shown in Table IV, 0.9 g, ammonia gas 8.5 g was introduced over four hours at 10° to 15° C. Acetone 130 g then was added, and the reaction mixture stirred for ten hours at 50° to 55° C. The reaction mixture was worked up as in Examples 1 to 6. The results are shown in Table IV.

TABLE IV

| Example No. | Cocatalyst | Yield of Triacetone amine | | |
|---|---|---|---|---|
| | | g | %$^1$ | %$^2$ |
| Control 1 | None (1.8 g of monobromoacetyl-bromide was used) | 48.6 | 62.7 | 80.1 |
| Example 18 | Ammonium chloride | 53.0 | 68.4 | 82.6 |
| Example 19 | Hydrazine dihydrochloride | 55.7 | 71.9 | 84.1 |
| Example 20 | Zinc chloride | 51.2 | 66.1 | 81.6 |
| Example 21 | Boron trifluoride (in ether) | 51.5 | 66.5 | 81.3 |

The effect of the cocatalyst in improving yield is apparent from the data in Table IV.

Having regard to the foregoing disclosure the following is claimed as the invention and patentable embodiments thereof:

1. A process for preparing triacetone amine which comprises reacting acetone and ammonia in the presence of a catalytically effective amount of an organic hydrocarbon carboxylic acid halide or organic halo-substituted hydrocarbon carboxylic acid halide selected from the group consisting of hydrocarbon mono and di carboxylic acid halides and halo-substituted hydrocarbon mono and di carboxylic acid halides having from two to about eighteen carbon atoms, and recovering triacetone amine from the reaction mixture.

2. A process according to claim 1 in which the organic group of the organic carboxylic acid halide is halo-substituted.

3. A process according to claim 1 in which the organic hydrocarbon carboxylic acid halide has the formula:

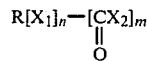

in which:
R is a hydrocarbon radical selected from the group consisting of aliphatic, cycloaliphatic and carboxylic aromatic radicals having from one to about seventeen carbon atoms;
$X_1$ and $X_2$ are selected from fluorine, chlorine, bromine, and iodine, and can be the same or different;
n is a number from 0 to 6; and
m is 1 to 2.

4. A process according to claim 1 in which the amount of organic carboxylic acid halide is at least 0.01% by weight of the acetonine.

5. A process according to claim 4 in which the amount is within the range from about 0.05% to about 10% by weight of acetonine.

6. A process according to claim 1 in which the organic carboxylic acid halide is acetyl chloride.

7. A process according to claim 1 in which the organic carboxylic acid halide is acetyl bromide.

8. A process according to claim 1 in which the organic carboxylic acid halide is chloroacetyl chloride.

9. A process according to claim 1 in which the organic carboxylic acid halide is bromoacetyl bromide.

10. A process according to claim 1 in which the organic carboxylic acid halide is bromopropionyl bromide.

11. A process according to claim 1 in which the organic carboxylic acid halide is benzoyl bromide.

12. A process according to claim 1 in which a co-catalyst reacting synergistically with the organic carboxylic acid halide is included in the reaction mixture.

13. A process according to claim 12 in which the co-catalyst is selected from the group consisting of elemental bromine and elemental iodine; lithium, sodium and potassium bromide and iodide; ammonium chloride, bromide and iodide; hydrazine chloride; pg,18 lithium and ammonium thiocyanate; maleic hydrazide; barium hydroxide; magnesium silicate hydrate aluminum silicate hydrate; boron trifluoride, zinc chloride and calcium chloride.

14. A process according to claim 12 in which the amount of co-catalyst is within the range from about 0.01% to about 10% by weight of the acetone.

15. A process according to claim 1 in which the reaction temperature is within the range from about 0° C. and the boiling point of the reaction mixture at atmospheric pressure.

16. A process according to claim 15 in which the reaction temperature is within the range from about 30° to about 60° C.

17. A process according to claim 1 in which an inert solvent having a boiling temperature about the selected reaction temperature is included in the reaction mixture.

* * * * *